United States Patent [19]

Lee et al.

[11] Patent Number: 5,753,234
[45] Date of Patent: May 19, 1998

[54] SINGLE-SHOT VACCINE FORMULATION

[75] Inventors: Hyeon-Kook Lee; Jung-Hwan Park, both of Daejeon; Nam-Sok Choi, Seoul; Myung-Jin Kim; Soo-Hyeon Kim, both of Daejeon, all of Rep. of Korea

[73] Assignee: LG Chemical Ltd., Seoul, Rep. of Korea

[21] Appl. No.: 613,830

[22] Filed: Mar. 11, 1996

[30] Foreign Application Priority Data

Mar. 16, 1995 [KR] Rep. of Korea ............ 1995-5424

[51] Int. Cl.$^6$ .......... A61K 39/29; A61K 39/12; A61K 39/02; A61K 39/002
[52] U.S. Cl. ............... 424/204.1; 424/227.1; 424/278.1; 424/279.1; 424/280.1; 424/234.1
[58] Field of Search ........... 424/278.1, 279.1, 424/280.1, 204.1, 234.1, 184.1; 435/174, 177, 180, 182

[56] References Cited

U.S. PATENT DOCUMENTS

| | | | |
|---|---|---|---|
| 4,338,335 | 7/1982 | McAleer et al. | 424/361 |
| 4,744,933 | 5/1988 | Rha et al. | 264/4.3 |
| 5,015,476 | 5/1991 | Cochrum et al. | 424/423 |
| 5,344,644 | 9/1994 | Igari et al. | 424/85.1 |
| 5,417,986 | 5/1995 | Reid et al. | 424/499 |
| 5,536,508 | 7/1996 | Canal et al. | 424/501 |

FOREIGN PATENT DOCUMENTS

| | | |
|---|---|---|
| 8807870 | 10/1988 | WIPO. |
| 9427718 | 12/1994 | WIPO. |
| 9522318 | 8/1995 | WIPO. |

OTHER PUBLICATIONS

Audibert et al., "Adjuvants: current status, clinical perspectives and future prospects", Immunology Today 14, 281–284 (1993).

Kimura et al., "Studies on the Adjuvant Effect of Water–in–oil–in–water (w/o/w) Emulsion of Sesame Oil", Japan. J. Exp. med. 48, 203–209 (1978).

Hyeon–Kook Lee, et al., "Double–walled microparticles for single shot vaccine", Journal of Controlled Release, 1997, pp. 283–293.

*Primary Examiner*—Marian C. Knode
*Assistant Examiner*—Donna C. Wortman
*Attorney, Agent, or Firm*—Anderson Kill & Olick, P.C.

[57] ABSTRACT

A microparticle having a particle size ranging from 0.5 to 300 μm, which is prepared by dissolving an antigen or a mixture of antigens in an aqueous solution, adding a water-soluble substance thereto, and removing water to obtain a core particle and coating the core particle with a biodegradable polymer; and a single-shot vaccine formulation prepared by dispersing the microparticles in an injection medium.

19 Claims, 1 Drawing Sheet

SINGLE-SHOT VACCINE FORMULATION

FIELD OF THE INVENTION

The present invention relates to microparticles having a particle size ranging from 0.5 to 300 μm, which are prepared by dissolving an antigen or a mixture of antigens in an aqueous solution, adding a water soluble substance thereto, and removing water to obtain a core particle and coating the core particle with a biodegradable polymer; and a vaccine formulation prepared by dispersing the microparticles in a medium for injection, which can accomplish the immunization effect against an infectious disease by administering a single injection only ("single-shot vaccine formulation") due to the delayed release of the antigen over a period of, e.g., several months.

BACKGROUND OF THE INVENTION

Hitherto, there have been developed a large number of vaccines effective in preventing various infectious diseases. However, most of the currently used vaccines require multiple inoculations, which requirement imposes an economical burden as well as inconveniences to the vaccinees(M. T. Aguado and P. H. Lambert, *Immunobiol.*, 184, 113(1992); Aryward, B., et al., *Vaccine*, 12, 1155(1994)). In particular, it has been found that only about 30% of those who receive the first inoculation return for the second administration. Statistically, therefore, only 9 out of 100 would complete an immunization process when three inoculations are prescribed, clearly demonstrating the need for a vaccine that can accomplish immunization by a single-shot inoculation.

The prior art approach to the development of a single-shot vaccine has basically centered on the idea of using a microparticle, wherein a desired antigen is encapsulated with a biodegradable polymeric material, which releases the antigen slowly over a prescribed time period to accomplish the vaccination(R. Langer and J. Folkman, *Nature*, 263, 797(1976)).

Among various biodegradable polymers, polylactide (PLA), polyglycolide(PGA), and poly(lactide-co-glycolide) (PLGA) are generally known to be safe because they undergo in vivo hydrolysis to harmless lactic acid and glycolic acid. Those polymers have been used in making a suture whose post-operation removal is not required; and also in formulating encapsulated leuprolide acetate, a LHRH analogue, which has been approved by FDA for human use(R. Langer and M. Mose, *Science*, 249, 1527 (1990); D. K. Gilding and A. M. Reed, *Polymer*, 20, 1459 (1979); and William Morris, et al., *Vaccine*, 12, 5(1994)). The degradation rates of these polymers vary with the glycolide/lactide ratio and molecular weight thereof, and, therefore, the release of the drug can be sustained over several months by adjusting the molecular weight and glycolide/lactide ratio of the polymer as well as the particle size, and coating thickness of the capsule formulation(S. J. Holland, et al., *J. control. Rel.*, 4, 155(1986)).

Since 1988, World Health Organization(WHO) has been sponsoring a number of studies to develop a single-shot vaccine for tetanus toxoid using the above-mentioned biodegradable polymers(M. T. Aguado, *Vaccine*, 11, 596(1993); Proceed. Intern. Symp. Control. Rel. Bioact. Mater, 21st, Controlled Release Society, Inc., Y. Men, et al., Paper No. 126(1994); 20th, B. Gander, et al., Paper No. 135(1993); 19th, A. M. Hazrati, et al., Paper No. 220(1992); 21st, M. Gilley, et al., Paper No. 218(1992); 21st, Manmohan Singh, et al., Paper No. 1476(1994); 21st, C. Yan, et al., Paper No. 127(1994)).

Notwithstanding these efforts, however, no single-shot vaccine formulation has been put to practical use mainly due to the deficiencies that the amount of antibody formed by the encapsulated formulation is only about 1/10 of that produced by a conventional alum formulation and that the result is not reproducible(R. E. Spier, *Vaccine*, 11, 1450(1993); M. T. Aguado and P. H. Lambert, *Immunobiol.*, 184, 113(1992)). The causes of these problems have been observed to be: first, an organic solvent used for dissolving the biodegradable polymer reduces or nullifies the antigenicity of the antigen by denaturing the antigen; secondly, when in contact with water, the antigen forms an aggregate which has a reduced antigenicity; and thirdly, the antigenicity is reduced or destroyed due to undesirable interactions between the antigen and the hydrophobic biodegradable polymer.

Alonso et al. prepared a single-shot vaccine by encapsulating tetanus toxoid with PLA and PLGA but only 0.5 to 20% of the original tetanus toxoid antigenicity was found to remain in the vaccine particle due to the unavoidable contact of the toxoid with an organic solvent in the encapsulation process(Maria J. Alonso, et al., *Vaccine*, 12, 299(1994)). In an experiment using a rat, the vaccine formulation revealed an antibody formation capacity much lower than a control using alum as an adjuvant without boosting, showing that this vaccine formulation is not viable as a single-shot vaccine. Schwendeman et al. endeavored to solve the above problem by chemical modification of the tetanus toxoid, i.e., by S-alkylating the thiol-groups of the antigen, but the result was unsatisfactory(S. P. Schwendeman, et al., *Proceed. Intern. Symp. Control. Rel. Bioact. Mater*, 21st, Paper No. 128, 1994).

Nellore et al. reported a single-shot vaccine formulation for hepatitis B which comprises microparticles prepared by encapsulating a hepatitis B surface antigen (HBsAg) with PGA by using a method involving organic solvent extraction or evaporation(R. V. Nellore, et al., *J. Parenteral Science & Technology*, 46, 176(1992)). Animal experiments using guinea pigs showed that a formulation comprising smaller particles in a size range of 1 to 10 μm exhibited an antibody formation capacity which was much lower than a control using alum as an adjuvant without boosting, while other formulations having particles ranging from 20 to 60 μm and from 1 to 60 μm were essentially inactive. In these formulations, HBsAg was denatured by the organic solvent used during the encapsulation process.

Therefore, in order to prepare an efficient single-shot vaccine by encapsulating an antigen with a biodegradable polymer, one must use a biodegradable polymer which does not require the use of an organic solvent in the encapsulating step, or the antigen must be prevented from contacting an organic solvent during the process. However, there has been no known biodegradable polymer which does not require such use of an organic solvent.

For the microparticles have been typically prepared by encapsulating an organic, peptide or protein drug with a biodegradable polymer. Specifically, an oily phase is prepared by dissolving or dispersing the drug in an organic solvent wherein a biodegradable polymer is dissolved, and preparing an oil-in-water("O/W") emulsion by dispersing the oily phase into an aqueous phase in the presence of a surfactant. Then, the organic solvent is removed by a conventional method, e.g., evaporation or extraction, to solidify the biodegradable polymer to obtain microparticles. At the end of the process, the drug exists to be dispersed in the polymer matrix and the resulting microparticles exist as a dispersion in the aqueous phase wherein a surfactant is dissolved. However, this conventional method has the drawbacks in that: most biodegradable polymers are apt to be hydrolyzed by water; surfactants are generally unsuitable for injection and, therefore, must be removed by a washing process; and the particles must be subjected to a drying process after the washing process to prevent the degradation of the polymer.

In this O/W emulsion method, the drug contacts directly with the organic solvent, and, therefore, the method cannot be applied for the preparation of a vaccine formulation comprising an antigen whose antigenicity may be reduced as a result of the contact. Further, the method has a further limitation in that it cannot be employed for a water-soluble drug. Consequently, development efforts have been shifted to the discovery of a method using a W/O/W emulsion to overcome the above problems.

For example, European Patent Application No. 87309286.0 discloses a vaccine formulation for oral administration comprising particles of 10 μm or less which are prepared by encapsulating various antigens with PLA, PGA, PLGA, etc. which are known to pass the Peyer's Patches.

Further, European Patent Application No. 88302940.7 discloses an injection formulation, which is capable of maintaining its effect over 6 months, by encapsulating a peptide or protein drug such as LHRH analog with a biodegradable polymer, e.g., PLGA. More specifically, the microparticles are prepared by: dissolving or dispersing the drug in an aqueous phase; mixing the aqueous phase with an organic solvent wherein a biodegradable polymer and a surfactant are dissolved to obtain a W/O emulsion; dispersing the W/O emulsion into an aqueous phase containing a surfactant to obtain a W/O/W emulsion; and then removing the organic solvent to prepare microparticles comprising the drug.

According to this method, the contact of the drug with the organic solvent can be reduced in comparison with the O/W emulsion method. However, a certain degree of mixing between the inner and outer aqueous phases cannot be prevented, which may result in a reduction of the antigenicity of the vaccine. Moreover, after a washing process to remove the surfactant, water in the inner aqueous phase is normally removed by a conventional method, e.g., lyophilization. A number of large pores may be formed in the biopolymer layer during this water removal process, and, in case of an encapsulated vaccine, these pores may act as conduits for water in human body, facilitating the formation of antigen aggregates with concomitant loss of antigenicity.

In order to overcome the above drawbacks, International Patent Publication No. WO 93/07861 discloses a process for preparing multi-phase particles, which comprises: producing a W/O/W emulsion using a highly viscous edible oil; replacing the outer aqueous phase with an acetonitrile solution of a biodegradable polymer such as PGA, PLA and PLGA; dispersing the resulting emulsion into a mineral oil; and removing acetonitrile to obtain multi-phase particles wherein a W/O microemulsion is encapsulated in a solid polymer shell. However, the process has the drawbacks in that: it is not possible to rid the finished multiphase particle of the surfactant, e.g., aluminum monostearate and Span80, which is used to increase the viscosity and dispersion stability of the edible oil thereby preventing the release of the drug from the inner aqueous phase into the outer aqueous phase; and the drug may loss its antigenicity during the process wherein the temperature is increased up to 140° C. to facilitate the dispersion of the emulsion.

The phase separation method(J. C. Wu et al., *J. Microencapsulation*, 11(3), 297–308(1994)) comprises dissolving a polymer in a first solvent; adding thereto a second solvent which does not dissolve the polymer but mixes with the first solvent; and, thereby, obtaining core-shell type microparticles formed by the solidification of the polymer around the drug as the solubility of the polymer decreases. However, like the O/W emulsion method, this method cannot prevent the antigen from contacting the second organic solvent.

Another problem associated with the above-mentioned methods using emulsions is the possible loss of activity of protein drugs. Proteins are apt to be denatured by a mechanical force, as in a high energy dispersion process. This is a serious problem considering that most antigens are proteins.

On the other hand, a spray drying method(B. Gander et al., *J. Microencapsulation*, 12(1), 83–97(1995)) comprises dissolving or dispersing a drug in an organic solvent wherein a biodegradable polymer is dissolved, and spray drying the mixture to obtain microparticles. However, this method also cannot avoid the direct contact of a drug with an organic solvent.

International Patent Publication No. WO 94/12158 and U.S. Pat. No. 5,019,400 suggest a freeze-and-extract method for preparing encapsulated protein drug(growth hormone) particles. In this method, the drug is dispersed in an organic solvent, e.g., methylene chloride, wherein a biodegradable polymer is dissolved and the solution is sprayed into a low-temperature liquid gas to form frozen particles. These particles are collected on the surface of frozen ethanol. As the frozen ethanol is melted, the frozen particles thaw and the organic solvent in the particle is extracted by ethanol, thereby forming microparticles encased in the solidified polymer. This method also allows the direct contact of the antigen with the organic solvent, and the release period of the drug is only several days. Therefore, this method is not suitable for the preparation of a single-shot vaccine which should release the antigen over a much longer period.

International Patent Publication No. We 92/14449 discloses a process for preparing particles containing a protein drug which comprises: dispersing a powdered protein drug in a molten fatty acid anhydride, cooling the mixture to solidify the mixture, and pulverizing the mixture to obtain particles. The fatty acid anhydride melts at a temperature ranging from 45° to 75° C. and does not denature a protein unlike a conventional organic solvent. However, in this process, the use of a fatty acid anhydride as the encapsulating material makes it difficult to obtain microparticles having a particle size suitable for injection. Further, the fatty acid anhydride itself is not capable of releasing a drug over a long time, and, therefore, it is not suitable for use in the preparation of a single-shot vaccine formulation.

European Patent Application No. 88113933.1 teaches an encapsulated particle formulation designed for a zero-order or bi-phasic mode of release of a protein drug, herbicide or fertilizer, which is prepared by: coating the drug, herbicide or fertilizer with an absorptive polymer and coating again the resulting particle with a polymer, which is insoluble in water but passes the drug, herbicide or fertilizer therethrough. However, the water-insoluble polymer used in the second coating, i.e., cellulose, is not a biodegradable polymer and it releases the drug for the duration of only one day in an uncontrollable manner. Further, the particle is rapidly infiltrated by water in human body and, therefore, in case that the drug is an antigen, it would lose its antigenicity by forming aggregates. Moreover, this process is not suitable for the preparation of microparticles for injection because the size of the first-coated particle ranges from 125 to 10000 μm and the second coating has to be thick enough to prevent its rupture by the swelling of the water-absorptive polymer used in the first coating.

As described above, there have been many attempts to develop a process for preparing a single-shot vaccine which avoids undesirable interactions of a protein drug with an organic solvent, a biodegradable polymer and water in human body. Despite these efforts, a method capable of adequatelyprotecting the antigenicity of an antigen during the process of encapsulating the antigen has not been found; and, accordingly, there has continued to exist a need to develop a single-shot vaccine formulation (William Morris, et al., *Vaccine*, 12, 5(1994)).

SUMMARY OF THE INVENTION

Accordingly, it is an object of the present invention to provide microparticles comprising an intact antigen or a mixture of antigens encapsulated in a polymer.

Another object of the present invention is to provide a single-shot vaccine formulation prepared by dispersing the microparticles in a medium for injection.

In accordance with the present invention, there is provided microparticles having an average particle size ranging from 0.5 to 300 µm, which is prepared by dissolving an antigen or a mixture of antigens in an aqueous solution, adding a water soluble substance thereto, and removing water to obtain a core particle and coating the core particle with a biodegradable polymer; and a single-shot vaccine formulation prepared by dispersing the microparticles in a medium for injection, which can accomplish the immunization against an infectious disease by only one injection.

BRIEF DESCRIPTION OF THE DRAWING

The above and other objects and features of the present invention will become apparent from the following description of the invention, when taken in conjunction with FIG. 1, which shows the relationship between the particle property and antibody formation, wherein three vaccine formulations prepared in accordance with the present invention are compared with a conventional alum formulation.

DETAILED DESCRIPTION OF THE INVENTION

Figure 1:
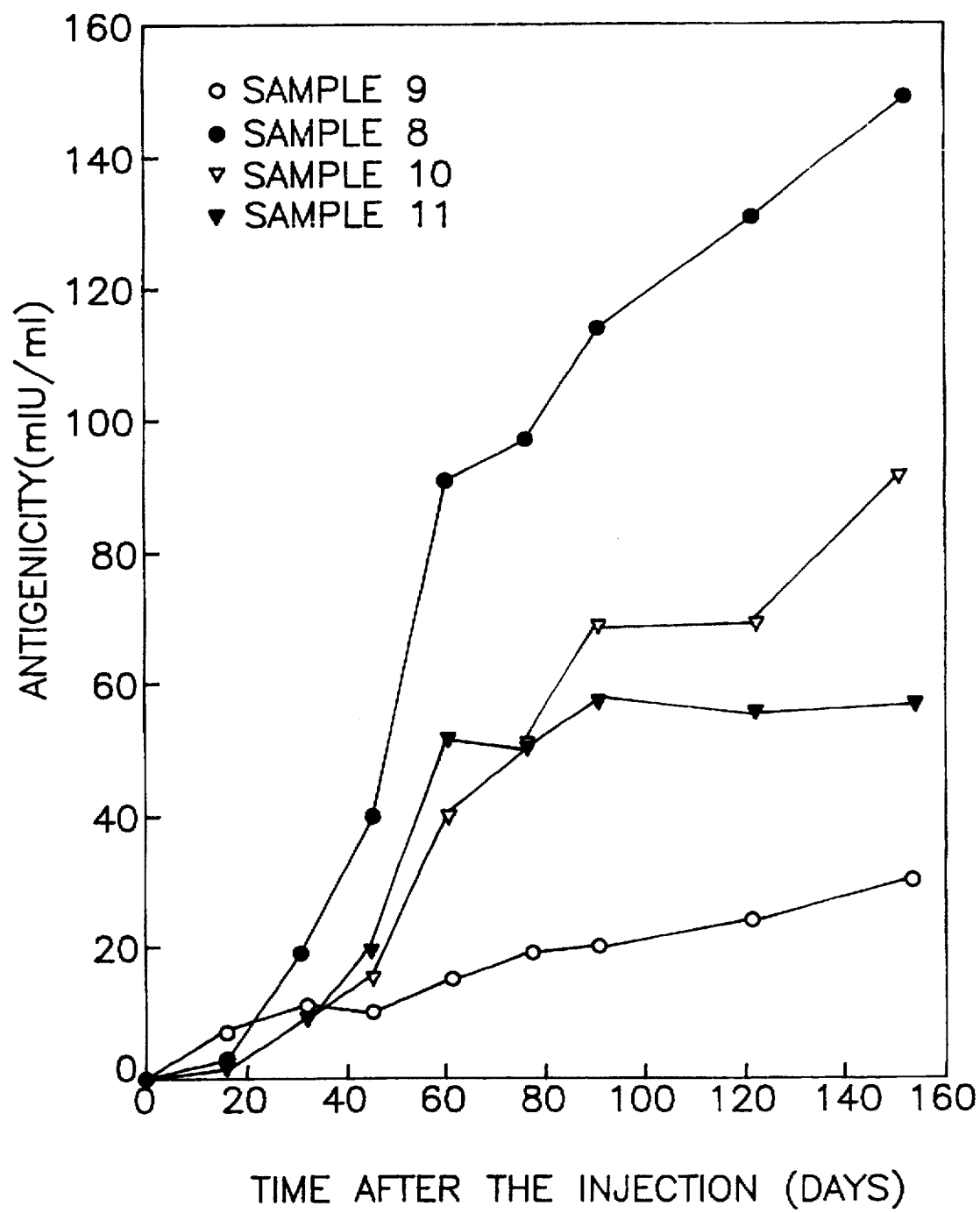

All references cited herein are hereby incorporated in their entirety by reference.

The microparticle of the present invention is prepared by dissolving an antigen in an aqueous solution, adding a water soluble substance thereto, and removing water to obtain a powdered particle("a core particle") and coating the core particle with a hydrophobic biodegradable polymer to obtain the final microparticle. The microparticle has a spherical or spheroidal shape with a size ranging from 0.5 to 300 µm. A single-shot vaccine formulation, which can accomplish the vaccination by only one injection, may be prepared by dispersing the microparticle in an injection medium.

A suitable antigen which may be used in the present invention is an attenuated, killed or recombinant antigen which is used as a vaccine for a single disease("single antigen") or two or more diseases simultaneously("mixed antigen"). The mixed antigen may be a mixture of two or more antigens, or an antigen which has antigenicities for two or more diseases simultaneously, e.g., a recombinant protein. As an antigen, there may be used an entire organism, e. g., a viral or bacterial whole cell, or a part of the organism, e. g., a certain protein having an antigenicity.

Exemplary antigens obtained from or directed against the pathogen responsible of the present invention include antigens for hepatitis, diphtheria, chickenpox, typhoid, pertussis, tetanus, tuberculosis, salmonellosis, cholera, herpes, yellow fever, measles, poliomyelitis, rubella, mumps, rabies, plague, schistosomiasis, influenza, trypanosomiasis, leishmaniasis, leprosy, meningitis, and malaria. More specifically, they include hepatitis B surface antigen, tetanus toxoid, Staphylococcal enterotoxin B toxoid, ricin toxoid, and attenuated influenza virus.

The core particle is prepared by dissolving or dispersing the antigen in a solution obtained by dissolving a water-soluble substance in a suitable aqueous solvent, e. g., water or a buffer, and drying the mixture by a spray drying or a freeze drying method. A suitable adjuvant may be added to the solution, if necessary, and examples thereof include alum; muramyl dipeptide, muramyl tripeptide and derivatives thereof; tymosin alpha; monophosphoryl lipid A; saponin; an immunostimulating complex; a polyelectrolyte such as a copolymer of polyoxyethylene and polyoxypropylene; and a mixture thereof.

The water-soluble substance used for the preparation of the core particle does not bring about an undesirable interaction with the protein antigen and is practically insoluble in the organic solvent used in the coating step. Exemplary water-soluble substances include water-soluble saccharides such as glucose, xylose, galactose, fructose, lactose, maltose, saccharose, alginate, dextran, hyaluronic acid, chondroitin sulfate and water-soluble cellulose derivatives, e.g., hydroxypropylmethyl cellulose, hydroxypropyl cellulose(HPC), carboxymethyl cellulose(CMC) and sodium carboxymethyl cellulose(CMC-Na); proteins such as albumin and gelatin; amino acids such as glycine, alanine, glutamic acid, arginine, lysine and a salt thereof; and a mixture thereof; while HPC, CMC, CMC-Na, gelatin, and a mixture thereof are preferred.

The water-soluble substance may be used in an amount ranging from 1 to 50, preferably, from 5 to 15 times the weight of total antigen.

The core particle so prepared has a particle size ranging from 0.1 to 200 µm, preferably, from 0.5 to 20 µm. In order to prepare the final microparticle, the core particle is dispersed in an organic solvent, wherein a hydrophobic biodegradable polymer is dissolved, by using a suitable apparatus, e.g., a magnetic stirrer, homogenizer, microfluidizer and sonicator.

The biodegradable polymer is used in an amount ranging from 1 to 100, preferably, from 5 to 30 times the weight of the core particle. The coating of the core particle is made of a water-soluble substance which is insoluble in the organic solvent, and therefore, it prevents the reduction or loss of the antigenicity of the antigen by blocking the contact of the antigen with the organic solvent.

Exemplary hydrophobic biodegradable polymers which may be used in the present invention include poly(lactide-co-glycolide)(PLGA), polyglycolide(PGA), polylactide (PLA), copolyoxalates, polycaprolactone, poly(lactide-co-caprolactone), polyesteramides, polyorthoesters, poly($\beta$-hydroxybutyric acid), and polyanhydride; while PLGA and PLA are preferred.

Any of the organic solvents well-known in the art may be used to dissolve the biodegradable polymer and these include carbon tetrachloride, methylene chloride, acetone, chloroform, ethyl acetate and acetonitrile.

The microparticle of the present invention is composed of the core particle coated with a biodegradable polymer, and is obtained from an organic suspension wherein the core particle is evenly dispersed in an organic solution of a biodegradable polymer("the core particle dispersed system"). The core particle dispersed system is advantageous in that a microparticle can be prepared therefrom in accordance with a conventional method, while avoiding the contact of the antigen with the organic solvent or with the biodegradable polymer. Further, the surface area of the core particle in contact with the organic solvent is sufficiently low such that a physical contact of the antigen with the organic solvent may not be occurred.

Specifically, the microparticle of the present invention may be prepared from the core particle dispersed system in accordance with any one of the following conventional methods.

1) Solvent evaporation method

This method is well known for the preparation of a microparticle, but the present invention differs from the prior arts in that the core particle dispersed system, wherein the contact of the antigen with the organic solvent is prevented, is employed in place of an aqueous solution wherein the antigen is dissolved or dispersed.

Specifically, the microparticle may be prepared by dispersing the core particle dispersed system in an aqueous solution comprising a surfactant to obtain an O/W emulsion and then removing the organic solvent from the core particle dispersed system, or by dispersing the core particle dispersed system in a solvent, which is immiscible with the core particle dispersed system and is a nonsolvent for the biodegradable polymer, to prepare an O/O emulsion and removing the organic solvent from the core particle dispersed system. When acetonitrile is used as the organic solvent of the core particle dispersed system, a mineral oil can be used as the solvent which is immiscible with the core particle dispersed system and is a nonsolvent for the biodegradable polymer.

2) Solvent extraction method

This method is also well-known in the art for the preparation of a microparticle, but the present invention differs from the prior arts in that the core particle dispersed system is employed. Specifically, the microparticle may be prepared by extracting the organic solvent of the core particle dispersed system by using a solvent, which is immiscible with the core particle dispersed system and is a nonsolvent for the biodegradable polymer, such as a mineral oil and paraffin oil.

3) Rapid freezing and solvent extraction method

The present invention is different from the prior arts in that the core particle dispersed system is employed. Specifically, the core particle dispersed system is sprayed into a low-temperature liquid gas phase using an ultrasonic apparatus to form a frozen particle. This particle is collected on the surface of frozen ethanol. As the frozen ethanol is melted, the frozen particle thaws and the organic solvent in the particle is extracted into the ethanol phase with concomitant formation of a microparticle coated with the biodegradable polymer.

4) Spray drying method

This method is most preferable for use in the present invention and, specifically, the microparticle is prepared by spraying the core particle dispersed system by employing a spray-dryer. This method is advantageous due to its high productivity and rapidity. Further, it is also advantageous in that removal of water is unnecessary because water is not used in the process; no surfactant is required; and the washing and drying processes can be omitted.

The particle size of the microparticle thus prepared ranges from 0.5 to 300 μm, preferably, from 1 to 180 μm. Those microparticles having a particle size smaller than 180 μm may be dispersed in an injection medium to prepare an injection formulation for subcutaneous, intramuscular, and intraperitoneal injections. Those particles having a particle size larger than 180 μm may be used for preparing a formulation for oral administration.

Therefore, the present invention further provides a single-shot vaccine formulation which is prepared by dispersing the microparticles in a suitable injection medium. The vaccine formulation may comprise single antigen alone, or two or more kinds of antigens together. The vaccine formulation comprising two or more antigens may be prepared by employing core particles comprising a mixture of two or more kinds of antigens, or by employing a mixture of two or more kinds of core particles each comprising an antigen different from each other.

The single-shot vaccine formulation of the present invention can accomplish a vaccination against the antigen comprised therein by only one injection and the amount of antigen in the vaccine formulation is the same or less than that of the conventional alum formulation which needs several injections to accomplish the vaccination.

Exemplary injection media which can be used in the present invention include a buffer with or without dispersing agents and/or preservatives, an edible oil, mineral oil, cod liver oil, squalene, squalane, mono-, di- or triglyceride and a mixture thereof; said edible oil being corn oil, sesame oil, olive oil, soybean oil, safflower oil, cotton seed oil, peanut oil or a mixture thereof.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

The materials and methods used in the Examples are as follows:

Antigen

A recombinant hepatitis B surface antigen(HBsAg) dissolved in a phosphate buffered saline(PBS), which is prepared in accordance with the method of Korean Patent Publication No. 93-2735(Publication date: Apr. 9, 1994).

Biodegradable polymer

PLGA(50/50) produced by BPI, U.S.A.

Amount of antigen: Determined by Lowry method.

Antigenicity: Determined by using AUZYME test kit (Abbott, U.S.A).

Antibody titer

Geometric average of titers obtained from the sera of 11 guinea pigs by using AUSAB test kit(Abbott, U.S.A).

Guinea pig

Those weighing 300–400 g and confirmed not to have antibodies in their blood 2 days before the administration of sample. Blood is collected from the heart of the guinea pig by using the cardiac puncture technique.

EXAMPLE 1

Preparation of Core particle by Using Freeze Drying Method

Recombinant HBsAg was dissolved in 10 mM PBS to a concentration of 300 μg/ml and hydroxypropyl cellulose was added thereto to a concentration of 0.3 mg/ml(Sample 1), 1.5 mg/ml(Sample 2), and 3.0 mg/ml(Sample 3), respectively. Each solution was frozen at −700° C. for 30 minutes by using dry ice and acetone, and then freeze dried for 24 hours by using EYELA FD-81 freeze dryer(Tokyo Rikakikai, Japan) at 0.05 torr and a condenser temperature of −80° C. to obtain core particles comprising HBsAg dispersed in hydroxypropyl cellulose. The average particle sizes of the core particles thus prepared were 1.0, 1.2 and 1.5 μm, respectively.

EXAMPLE 2

Preparation of Core particle by Using Spray Drying Method

Recombinant HBsAg was dissolved in 10 mM PBS to a concentration of 300 μg/ml, and each of hydroxypropyl cellulose(Sample 4), sodium carboxymethyl cellulose (Sample 5) and gelatin(Sample 6) was added thereto to a concentration of 3.0 mg/ml. Each solution was provided to a spray dryer(Buchi 190) at a flow rate of 3 ml/minute to obtain core particles comprising HBsAg dispersed in hydroxypropyl cellulose, sodium carboxymethyl cellulose, and gelatin, respectively. In this step, the flow rate of propellant nitrogen was 600 l/minute and the inflow air temperature was 70° C. The average particle sizes of the core particles thus prepared were 4.6, 6.3 and 4.9 μm, respectively.

Test Example 1

Protection of Antigen in Core particle

To confirm whether the core particle comprising HBsAg dispersed in the water-soluble substance protects the antigenicity of the antigen therein from the contact with the organic solvent, the core particles prepared in Example 1 and 2 were dispersed in ethyl acetate or acetonitrile, which dissolves PLGA but not hydroxypropyl cellulose, and the resulting solutions were mixed by using a magnetic stirrer to allow the core particle to contact the organic solvent. The core particles were separated and dried to remove the organic solvent. The dried core particles were dissolved in a buffer(10 mM phosphate, pH 7.5) and the antigenicity was determined by AUZYME kit and compared to that of recombinant HBsAg solution of Korean Patent Publication No. 93-2735 stored in a cryogenic state.

Further, the HBsAg alone was used as a control, as follows. Recombinant HBsAg was dissolved in 10 mM PBS to a concentration of 300 μg/ml and to the solution was added a same volume of each of various organic solvents listed in Table 1. The resulting solutions were mixed by using a magnetic stirrer for 10 minutes. The aqueous phases were separated from the solutions and antigenicities thereof were determined according to the same procedure as above. The precipitate was separated, dried and added to PBS for the determination of the antigenicity. However, the precipitate was not dissolved in PBS due to denaturation thereof which resulted in an insoluble form.

As a result, the antigen in the core particle which is comprising HBsAg dispersed in hydroxypropyl cellulose maintained its antigenicity after its contact with the organic solvent, while the antigen alone lost its antigenicity completely after its contact with the organic solvent.

TABLE 1

| Sample No. | Water-soluble polymer | Organic solvent | Antigenicity (%) | Insoluble ppt. | Note |
|---|---|---|---|---|---|
| Original HBsAg Solution | — | — | 100 | — | — |
| 1 | hydroxypropyl cellulose (0.3 mg/ml) | acetonitrile | 78 | — | — |
| | | ethyl acetate | 75 | — | — |
| 2 | hydroxypropyl cellulose (1.5 mg/ml) | acetonitrile | 80 | — | — |
| | | ethyl acetate | 80 | — | — |
| 3 | hydroxypropyl cellulose (3.0 mg/ml) | acetonitrile | 91 | — | — |
| | | ethyl acetate | 88 | — | — |
| 4 | hydroxypropyl cellulose (3.0 mg/ml) | ethyl acetate | 90 | — | — |
| 5 | sodium carboxymethyl cellulose (3.0 mg/ml) | | 85 | — | — |
| 6 | gelatin (3.0 mg/ml) | | 82 | — | — |
| Control | not used | acetonitrile | 0 | formed | — |
| | | ethyl acetate | 0 | formed | — |
| | | carbon tetrachloride | 0 | formed | — |
| | | chloroform | <<1.0 | formed | *1 |
| | | methylene chloride | <<1.0 | formed | *1 |
| | | benzene | <<1.0 | formed | *1 |
| | | hexane | <<1.0 | formed | *1 |

*1 trace amount was redissolved.

EXAMPLE 3

Preparation of Microparticles

PLGA(50/50) was dissolved in ethyl acetate to a concentration of 1% and the core particle of Sample 3 prepared in Example 1 was dispersed therein to a concentration of 1 mg/ml. The resulting solution was provided to a spray dryer(Buchi 190) at a flow rate of 3 ml/minute to obtain the final microparticles which were coated further with PLGA. In this step, the flow rate of nitrogen was 600 l/minute and the inflow air temperature was 60° C.

The average particle size of the microparticles thus prepared was 7 μm and the weight ratio of PLGA/the core particle was 10. The amount of antigen determined by Lowry method was 6 μg protein/mg of particle.

EXAMPLE 4

Preparation of Microparticles

Microparticles coated with PLGA were prepared by using Sample 4 of Example 2 as the core particle, in accordance with the same procedures as described in Example 3. The weight ratio of PLGA/the core particle was 10.

The average particle size of the microparticles thus prepared was 9μm and the amount of antigen was 3 μg protein/mg of particle.

EXAMPLE 5

Preparation of Microparticles

Sample 4 of Example 2 was dispersed in ethyl acetate to a concentration of 2 mg/ml, and microparticles coated with PLGA were prepared in accordance with the same procedures as described in Example 3. The weight ratio of PLGA/the core particle was 5.

The average particle size of the microparticles thus prepared was 7 μm and the amount of antigen was 6 μg protein/mg of particle.

EXAMPLE 6

Preparation of Microparticles

Sample 4 of Example 2 was dispersed in ethyl acetate to a concentration of 0.5 mg/ml, and microparticles coated with PLGA were prepared in accordance with the same procedures as described in Example 3. The weight ratio of PLGA/the core particle was 20.

The average particle size of the microparticles thus prepared was 10 μm and the amount of antigen was 1.5 μg protein/mg of particle.

EXAMPLE 7

Preparation of Microparticles 5 mg of Sample 4(the core particle) prepared in Example 2 was dispersed in 1 ml of ethyl acetate, wherein 200 mg of PLGA was dissolved, by using an ultrasonicator. The core particle dispersed system was mixed with 1 ml of 1% aqueous polyvinylalchol(PVA) solution by using a magnetic stirrer and the resulting mixture was dispersed in 100 ml of 0.3% aqueous PVA solution to obtain an O/W emulsion. The emulsion was mixed continuously for 5 hours to evaporate ethyl acetate and microparticles thus formed were separated by using a 0.5 μm filter, washed and then dried.

The average particle size was 110 μm.

Test Example 2

In vivo Effect of Water-Soluble Substance

The microparticle prepared in Example 3 was dispersed in PBS(Sample 7), and Sample 7 was injected once intraperitoneally to guinea pigs in a quantity that the amount of antigen becomes 40 μg protein/head. Blood samples were taken from the guinea pigs for 2 months after the injection at fifteen-day intervals and the concentration (mIU/ml) of formed antibody in each sample was determined.

As a control, particles coated with PLGA alone without a water-soluble substance was prepared as follows. Original HBsAg solution was frozen in accordance with the method of Example 1 without using a water-soluble substance and the HBsAg particles coated directly with PLGA alone (Comparative sample) were prepared therefrom in accordance with the method of Example 3. The Comparative sample was administered to guinea pigs in accordance with the same method as above, and then the concentration of formed antibody was determined.

As a result, Sample 7 showed an antibody concentration higher than that of Comparative sample, as can be seen from Table 2. This result shows that, without a water-soluble substance, the antigen lost its antigenicity due to the undesirable interactions of the antigen with the organic solvent and the biodegradable polymer.

TABLE 2

| Sample | Ab Conc. (mIU/ml) Time After the Injection (Months) | | | | |
|---|---|---|---|---|---|
| | 0 | 0.5 | 1 | 1.5 | 2 |
| Sample 7 | 0.0 | 2.4 | 10.6 | 24.6 | 34.0 |
| Comparative sample | 0.0 | 1.1 | 8.1 | 10.2 | 14.3 |

Test Example 3
In vivo Effect of Single-Shot Vaccine Formulation

The following experiment was carried out to confirm if the vaccine formulation of the present invention has a superior effect as a single-shot vaccine formulation.

The microparticles prepared in Example 5 were dispersed in 1.0 ml of an injection medium(PBS containing 0.02 wt % of Tween 80) to form a vaccine formulation(Sample 8), which was injected once subcutaneously to guinea pigs by using a 26 G syringe in a quantity that the amount of antigen becomes 20 μg protein/head. Blood samples were taken from the guinea pigs for 5 months after the injection at fifteen-day or a month intervals and the concentration(mIU/ml) of formed antibody in each sample was determined.

A comparative formulation which employs alum as an adjuvant was prepared as follows. PBS containing HBsAg and an alum dispersion solution(Superfos Biasector, Vedbaek, Denmark) were mixed to prepare a vaccine formulation containing HBsAg in an amount of 10 μg protein/ 1.5 mg alum.

The vaccine formulation was injected once to two groups of guinea pigs by using a 26 G syringe in a quantity that the amount of the antigen becomes 10 μg protein/ml/injection (primary injection). Thereafter, one group was subjected to the first boosting using the same antigen amount fifteen days after the primary injection(Comparative Example 1). The other group was further subjected to the second boosting 1.5 months after they received the first boosting in accordance with the same procedures as above(Comparative Example 2).

Further, one more group of guinea pigs were received a primary injection only by using the alum formulation and the same method as above, in a quantity that the amount of the antigen becomes 20 μg protein/ml/injection (Comparative Example 3, Sample 9).

The concentrations(mIU/ml) of formed antibody of Comparative Examples 1, 2 and 3 were determined as above and the results were compared with that of Sample 8.

The result is shown in Table 3, wherein it can be seen that the concentration of antibody formed by an injection of Sample 8 is higher than those formed by injections up to three times of the alum formulation. This result shows that the vaccine formulation of the present invention has a superior effect as a single-shot vaccine formulation, i.e., a single injection of the inventive vaccine formulation using 20 μg protein shows a superior vaccination effect than three injections of the alum formulation using 30 μg of protein.

TABLE 3

| Sample | Ab Conc. (mIU/ml) Time After the Injection (Months) | | | | | | | | |
|---|---|---|---|---|---|---|---|---|---|
| | 0 | 0.5 | 1 | 1.5 | 2 | 2.5 | 3 | 4 | 5 |
| Sample 8 | 0.0 | 2.5 | 18.9 | 40.0 | 90.0 | 97.0 | 113.0 | 132.5 | 149.4 |
| Comparative Example 1 | 0.0 | 3.3 | 9.6 | 30.6 | 72.0 | 86.0 | 86.0 | 108.6 | 131.5 |
| Comparative Example 2 | 0.0 | — | 18.0 | — | 92.2 | — | 99.8 | — | — |
| Comparative Example 3 (Sample 9) | 0.0 | 6.8 | 10.7 | 9.2 | 14.4 | 18.0 | 19.5 | 22.0 | 30.2 |

Test Example 4
Relationship between the Particle Property of the Vaccine Formulation and Antibody Formation In order to investigate whether the time and amount of antibody formation are controllable in accordance with the weight ratio of the biodegradable polymer and the core particle, the following test was carried out.

Each of the microparticles prepared in Examples 4, 5 and 6 was suspended in PBS to prepare a single-shot vaccine formulation(Samples 10, 8 and 11), which was injected once subcutaneously to guinea pigs in a quantity that the amount of antigen becomes 20 μg protein/ head. Blood samples were taken from the guinea pigs for 5 months after the injection at fifteen-day intervals and the concentration(mIU/ml) of formed antibody in each sample was determined.

Further, the alum formulation prepared in Test Example 3 was injected once to guinea pigs in a quantity that the amount of antigen becomes 20 μg protein/head(Sample 9) and the concentration(mIU/ml) of formed antibody was determined in accordance with the same method as above.

The antibody concentration changes with time after the injection are shown in FIG. 1, wherein Sample 8, which has a PLGA/core particle weight ratio of 5, shows the highest rate of increase in the antibody concentration. Therefore, it was confirmed that the rate of antibody formation is controllable by regulating the thickness of the biodegradable polymer coating. Therefore, a single-shot vaccine containing mixed antigens or a single-shot vaccine which can release an antigen in different patterns can be prepared by using various particles having different properties.

As described in the above Examples, the single-shot vaccine formulation of the present invention can accomplish vaccination by administering only one injection and further has a higher antibody forming capacity than conventional vaccine formulations.

While the invention has been described with respect to the above specific embodiments, it should be recognized that various modifications and changes may be made to the invention by those skilled in the art which also fall within the scope of the invention as defined by the appended claims.

What is claimed is:

1. A microparticle having a particle size ranging from 0.5 to 300 μm, which is prepared by dissolving an antigen or a mixture of antigens in an aqueous solution, adding a water-soluble substance thereto, and removing water to obtain a core particle and coating the core particle with a biodegradable polymer.

2. The microparticle of claim 1, wherein the antigen is an attenuated, killed or recombinant antigen.

3. The microparticle of claim 1, wherein the core particle further comprises an adjuvant or an inorganic salt.

4. The microparticle of claim 1, wherein the antigen is obtained from or directed against the pathogen responsible for one or more of diseases selected from the group consisting of: hepatitis, diphtheria, chickenpox, typhoid, pertussis, tetanus, tuberculosis, salmonellosis, cholera, herpes, yellow fever, measles, poliomyelitis, rubella, mumps, rabies, plaque, schistosomiasis, influenza, trypanosomiasis, leishmaniasis, leprosy, meningitis, and malaria.

5. The microparticle of claim 3, wherein the adjuvant is alum; muramyl dipeptide, muramyl tripeptide and derivatives thereof; tymosin alpha; monophosphoryl lipid A; saponin; an immunostimulating complex; a polyelectrolyte; or a mixture thereof.

6. The microparticle of claim 1, wherein the water-soluble substance is used in an amount ranging from 1 to 50 times the weight of the antigen.

7. The microparticle of claim 1, wherein the water-soluble substance is a saccharide, a protein, an amino acid or a mixture thereof.

8. The microparticle of claim 7, wherein the saccharide is a cellulosic polymer, glucose, xylose, galactose, fructose, lactose, maltose, saccharose, alginate, dextran, hyaluronic acid, chondroitin sulfate or a mixture thereof.

9. The microparticle of claim 8, wherein the cellulosic polymer is hydroxypropyl cellulose, hydroxypropylmethyl cellulose, carboxymethyl cellulose, sodium carboxymethyl cellulose or a mixture thereof.

10. The microparticle of claim 7, wherein the protein is gelatin, albumin or a mixture thereof.

11. The microparticle of claim 7, wherein the amino acid is glycine, alanine, glutamic acid, arginine, lysine, or a salt or a mixture thereof.

12. The microparticle of claim 1, wherein the particle size of the core particle ranges from 0.1 to 200 μm.

13. The microparticle of claim 1, wherein the biodegradable polymer is used in an amount ranging from 1 to 100 times the weight of the core particle.

14. The microparticle of claim 1, wherein the biodegradable polymer is polyglycolide, polylactide, poly(lactide-co-glycolide) or a mixture thereof.

15. The microparticle of claim 1, wherein the biodegradable polymer is copolyoxalate, polycaprolactone, poly(lactide-co-caprolactone), polyesteramide, polyorthoester, poly(β-hydroxybutyric acid), polyanhydride or a mixture thereof.

16. A single-shot vaccine formulation prepared by dispersing microparticles recited in any one of claims 1 to 15 in an injection medium.

17. The single-shot vaccine formulation of claim 16, wherein the injection medium is a buffer which optionally contains a dispersing agent and/or a preservative.

18. The single-shot vaccine formulation of claim 17, wherein the injection medium is an edible oil, mineral oil, cod liver oil, squalene, squalane, mono-, di- or triglyceride, or a mixture thereof.

19. The single-shot vaccine formulation of claim 18, wherein the edible oil is corn oil, sesame oil, olive oil, soybean oil, safflower oil, cotton seed oil, peanut oil or a mixture thereof.

* * * * *

UNITED STATES PATENT AND TRADEMARK OFFICE
CERTIFICATE OF CORRECTION

PATENT NO. : 5,753,234
DATED : May 19, 1998
INVENTOR(S) : Hyeon-Kook Lee, et al

It is certified that error appears in the above-indentified patent and that said Letters Patent is hereby corrected as shown below:

On the title page

[30]    Foreign Application Priority Data

Mar. 16, 1995    [KR]   Rep. of Korea      95-5424

Signed and Sealed this

Twenty-first Day of July, 1998

Attest:

BRUCE LEHMAN

Attesting Officer        Commissioner of Patents and Trademarks